US012133858B2

United States Patent
Shin et al.

(10) Patent No.: US 12,133,858 B2
(45) Date of Patent: Nov. 5, 2024

(54) COMPOSITION FOR PROMOTING HAIR GROWTH AND IMPROVING, PREVENTING, OR TREATING HAIR LOSS CONTAINING 2'-FUCOSYLLACTOSE AS AN ACTIVE INGREDIENT

(71) Applicant: Advanced Protein Technologies Corp., Suwon-si (KR)

(72) Inventors: Chul Soo Shin, Suwon-si (KR); Jong Won Yoon, Seongnam-si (KR); Seon Min Jeon, Daegu (KR); Bo Mee Kim, Hwaseong-si (KR); Jeong Su Bang, Ansan-si (KR); Cheol Ho Jang, Hwaseong-si (KR); Eun Young Choi, Hwaseong-si (KR)

(73) Assignee: Advanced Protein Technologies Corp., Suwon-si (KR)

( * ) Notice: Subject to any disclaimer, the term of this patent is extended or adjusted under 35 U.S.C. 154(b) by 0 days.

(21) Appl. No.: 18/517,798

(22) Filed: Nov. 22, 2023

(65) Prior Publication Data
US 2024/0197763 A1   Jun. 20, 2024

Related U.S. Application Data

(63) Continuation of application No. PCT/KR2023/016584, filed on Oct. 24, 2023.

(30) Foreign Application Priority Data

Dec. 16, 2022 (KR) .......................... 10-2022-0177364

(51) Int. Cl.
| | | |
|---|---|---|
| *A61K 31/702* | (2006.01) | |
| *A23L 33/125* | (2016.01) | |
| *A61K 8/98* | (2006.01) | |
| *A61Q 7/00* | (2006.01) | |

(52) U.S. Cl.
CPC .......... *A61K 31/702* (2013.01); *A23L 33/125* (2016.08); *A61K 8/986* (2013.01); *A61Q 7/00* (2013.01)

(58) Field of Classification Search
CPC ..... A61K 31/702; A61K 8/986; A23L 33/125; A61Q 7/00
See application file for complete search history.

(56) References Cited

U.S. PATENT DOCUMENTS 6,645,477 B1 * 11/2003 Jarrousse ................. A61Q 7/00
                                                          435/183

FOREIGN PATENT DOCUMENTS

| JP | 2000-26248 A | 1/2000 | |
|---|---|---|---|
| JP | 2003-183133 A | 7/2003 | |
| KR | 10-1286266 B1 | 7/2013 | |
| KR | 20180102431 A * | 1/2018 | ............... C02F 1/52 |
| KR | 10-2018-0051688 A | 5/2018 | |
| KR | 20180051688 A * | 5/2018 | |
| KR | 10-2018-0102431 A | 9/2018 | |
| KR | 10-1953375 B1 | 2/2019 | |
| KR | 10-2042967 B1 | 11/2019 | |
| KR | 10-2097302 B1 | 4/2020 | |
| KR | 10-2021-0055900 A | 5/2021 | |
| KR | 10-2567042 B1 | 8/2023 | |
| WO | WO-2021061991 A1 * | 4/2021 | ........... A61K 31/702 |

OTHER PUBLICATIONS

Translation KR20180051688A (Year: 2024).*
Translation KR 2018010246A (Year: 2024).*
Korean Office Action for 10-2022-0177364, dated Feb. 28, 2023.
International Search Report issued Feb. 2, 2024 in Application No. PCT/KR2023/016584.

* cited by examiner

*Primary Examiner* — Michael P Cohen
(74) *Attorney, Agent, or Firm* — Sughrue Mion, PLLC

(57) ABSTRACT

Disclosed is a composition for promoting hair growth and ameliorating, preventing or treating hair loss containing 2'-fucosyllactose (2'-FL) as an active ingredient, and a method for promoting hair growth or ameliorating, preventing or treating hair loss, the method comprising administering to a subject in need thereof 2'-fucosyllactose. Treatment with a combination of testosterone and 2'-fucosyllactose increases hair gloss, increases hair length, reduces a hair loss area, enhances hair cuticles, increases the number and size of hair follicles, and improves expression of proteins and genes related to hair proliferation and growth, compared to treatment with testosterone alone, thus being applicable as a substance for various food and pharmaceutical compositions based on effects of promoting hair growth, improving hair loss, and ameliorating, preventing or treating hair loss.

4 Claims, 10 Drawing Sheets

COMPOSITION FOR PROMOTING HAIR GROWTH AND IMPROVING, PREVENTING, OR TREATING HAIR LOSS CONTAINING 2'-FUCOSYLLACTOSE AS AN ACTIVE INGREDIENT

CROSS REFERENCE TO RELATED APPLICATIONS

This application is a Rule 53 (b) Continuation of International Application No. PCT/KR2023/016584 filed Oct. 24, 2023, claiming priority based on Korean Patent Application No. 10-2022-0177364 filed Dec. 16, 2022, the respective disclosures of all of the above of which are incorporated herein by reference in their entirety.

BACKGROUND OF THE INVENTION

Field of the Invention

The present invention relates to a composition for promoting hair growth and ameliorating, preventing or treating hair loss containing 2'-fucosyllactose as an active ingredient and more specifically, to a food composition and a pharmaceutical composition that contain 2'-fucosyllactose as an active ingredient and thus have the effects of greatly promoting hair growth and ameliorating, preventing or treating hair loss by restoring the cuticle layer of hair. The present invention also relates to a method for promoting hair growth or ameliorating, preventing or treating hair loss, the method comprising administering to a subject in need thereof 2'-fucosyllactose.

Description of the Related Art

The hair cycle consists of anagen, which is a hair growth phase, catagen in which hair growth ends and hair bulb shrinks, telogen in which hair papilla ceases activity and the hair stays on the scalp, and exogen in which the dermal papilla begins to become active or forms new hair, causing old hair to be lost. This hair cycle varies from person to person and gender. In general, about 15% of all hair falls out and is regenerated during catagen and telogen.

Accordingly, when the amount of hair in telogen is 20% or more, it is considered to be excessive hair loss. Losing an average of 50 to 100 hairs per day is called "telogen effluvium", which is a physiologically normal hair loss phenomenon. However, losing hairs in amounts exceeding this range is suspected of male pattern baldness or alopecia areata.

There are various causes of hair loss and hair loss diseases include the highly frequent baldness (male pattern baldness) type androgenetic alopecia (androgenic alopecia), female pattern alopecia, alopecia areata, and telogen effluvium. In particular, male pattern baldness is known to be caused by genetic causes and male hormones and it is presumed that some female pattern baldness is caused by the same factors as male pattern baldness. Although alopecia is not a life-threatening disease, it greatly affects quality of life. Patients with alopecia suffer from severe social and mental stress due to external changes caused by hair loss. Particularly, as interest in beauty increases in modern society, the desire to overcome this is increasing.

Methods for treating hair loss include topical hair loss treatments such as minoxidil and oral hair loss treatments such as finasteride and dutasteride, but these treatments have the limitation in which the drugs are temporarily effective only when they are taken and problems of causing side effects (such as itching, sensitivity, and decreased d sexual function) in the human Another treatment is surgery such as scalp plastic surgery or hair transplant, but this method also has the problem of side effects and high surgical costs. Therefore, there is a need to develop substances that are safe for the human body and have no side effects while promoting hair growth and ameliorating, preventing or treating hair loss.

SUMMARY OF THE INVENTION

Therefore, the present disclosure has been made in view of the above problems and it is an object of the present invention to provide, as an alternative to conventional hair loss treatments, a food composition for promoting hair growth and ameliorating hair loss, or a pharmaceutical composition for promoting hair growth and preventing or treating hair loss, containing, as an active ingredient, 2'-fucosyllactose, which is a substance for treating hair loss that is safe for the human body and has no side effects. In addition, the present disclosure provides a method for promoting hair growth or ameliorating, preventing or treating hair loss, the method comprising administering to a subject in need thereof 2'-fucosyllactose.

In accordance with one aspect of the present invention, provided is a food composition for promoting hair growth or ameliorating hair loss containing 2'-fucosyllactose.

Preferably, the hair loss is androgenetic alopecia.

In accordance with another aspect of the present invention, provided is a pharmaceutical composition for promoting hair growth, or preventing or treating hair loss containing 2'-fucosyllactose.

Preferably, the hair loss is androgenetic alopecia.

Effect of the Invention

The present invention treats 2'-fucosyllactose to increase hair gloss, increase hair length, reduce a hair loss area, enhance hair cuticle, increase the number and size of hair follicles, and improve expression of proteins and genes related to hair proliferation and growth, compared to the group treated with testosterone alone, thus being applicable as a substance for various food and pharmaceutical compositions based on effects of promoting hair growth, improving hair loss, and ameliorating, preventing or treating hair loss.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
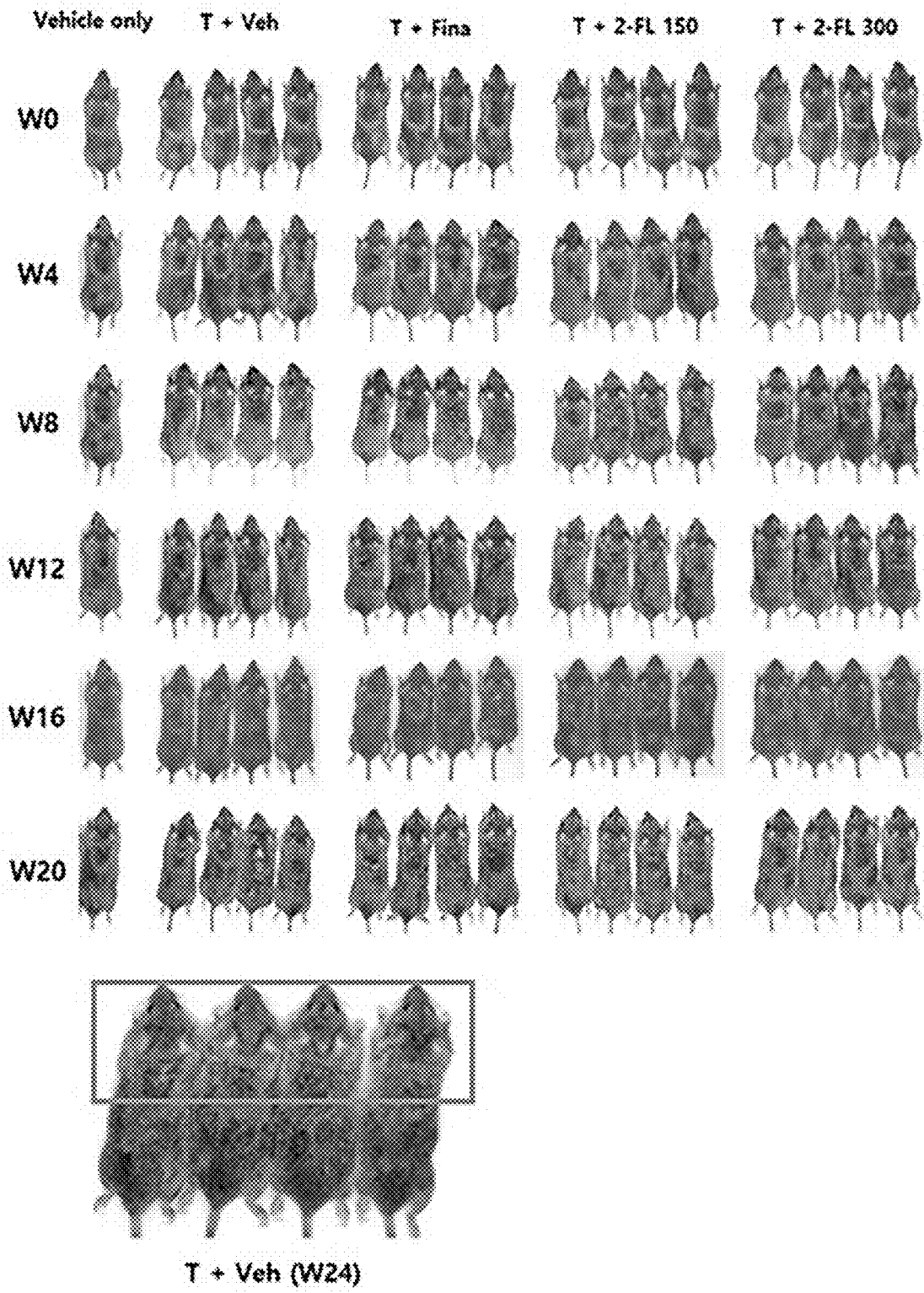
FIG. 1 is an image showing the hair of a mouse model treated with 2'-fucosyllactose according to the present invention.

Hereinafter, the present invention will be described in detail.

As interest in beauty increases in modern society, the desire to overcome hair loss is increasing. There are various causes of hair loss and hair loss diseases include the highly frequent baldness male pattern alopecia (androgenic alopecia), female pattern alopecia, alopecia areata, telogen effluvium and the like. In particular, genetic causes and male hormones are known to be major factors of androgenetic alopecia.

There are methods to treat hair loss such as drug treatment, scalp plastic surgery, and surgical procedures such as hair transplantation, but these methods are disadvantageously temporary, cause side effects on the human body, and are expensive. Accordingly, the present invention provides a composition for promoting hair growth and ameliorating, preventing or treating hair loss using a natural substance that is safe for the human body and has no side effects.

Accordingly, the present invention provides a food composition for promoting hair growth or ameliorating hair loss, containing 2'-fucosyllactose. In addition, the present invention provides a pharmaceutical composition for promoting hair growth, or preventing or treating hair loss containing 2'-fucosyllactose.

2'-fucosyllactose used in the present invention is a representative human milk oligosaccharide (HMO) contained in breast milk. According to the present invention, in vivo experiments show that 2'-fucosyllactose is effective in promoting hair growth or ameliorating, preventing, or treating hair loss. The hair loss is preferably male-pattern alopecia and male-pattern alopecia is generally considered to be caused by the production of high concentrations of male hormones, that is, androgens, in the blood. In particular, testosterone is converted into dihydrotestosterone (DHT), which is a more potent androgen, by 5α-reductase. Dihydrotestosterone (DHT) is known to be an androgen that causes hair loss.

Accordingly, according to one embodiment of the present invention, 2'-FL is administered at various concentrations (low and high concentrations) to mouse models randomly excessively treated with testosterone and analysis of the resulting hair change (observation of external phenotypes, measurement of length and hair loss area, and analysis of cuticle layer) and skin tissue analysis (observation of dyeing and confirmation of expression behaviors of hair growth-related marker proteins and hair growth-related factor genes in skin tissue) are performed. The results show treatment with 2'-FL is highly effective in promoting hair growth and ameliorating, preventing or treating hair loss.

Meanwhile, the food composition of the present invention may include any one selected from meat, cereals, caffeinated beverages, general beverages, chocolate, breads, snacks, confectioneries, pizza, jelly, noodles, gums, ice cream, alcoholic beverages, liquors, vitamin complexes and other health supplements, but is not limited thereto.

The content of 2'-fucosyllactose in the food composition of the present invention is not particularly limited and may vary depending on the condition of the subject to which the composition is administered, the type of specific disease, the degree of progression of the disease, and the like. If necessary, the content of 2'-fucosyllactose may be equal to the total content of the food. In the present invention, 2'-fucosyllactose is administered orally to a mouse model, as a subject, at 150 to 300 mg/kg mouse/100 μl based on the content of the control.

When the food composition of the present invention is used in the form of a food additive, it may be added alone or used in combination with other food or food ingredients, and may be appropriately used according to a conventional method.

Meanwhile, the pharmaceutical composition according to the present invention may further contain a pharmaceutically acceptable carrier, diluent or excipient. The carrier, excipient or diluent includes at least one selected from lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil. In addition, when the therapeutic and preventive agent is a drug, the pharmaceutical composition may further contain a filler, an anticoagulant, a lubricant, a wetting agent, a fragrance, an emulsifier, a preservative or the like.

Meanwhile, the pharmaceutical composition according to the present invention may be formulated into a preferred form depending on the method of use, and in particular, the pharmaceutical composition is preferably formulated by adopting a method well-known in the art to provide rapid, sustained or delayed release of the active ingredient after administration to a mammal. Specific examples of the formulation include any one selected from plasters, granules, lotions, liniments, lemonades, aromatic waters, powders, syrups, ophthalmic ointments, liquids and solutions, aerosols, extracts, elixirs, ointments, fluidextracts, emulsions, suspensions, decoctions, infusions, ophthalmic solutions, tablets, suppositories, injections, spirits, cataplasma, capsules, creams, troches, tinctures, pastes, pills, and soft or hard gelatin capsules.

Meanwhile, in the pharmaceutical composition of the present invention, the dosage may be determined in consideration of the administration method, the age, gender and weight of the patient, the severity of the disease and the like. For example, the pharmaceutical composition may be orally administered one or more times at 0.01 to 500 mg/kg (body weight), preferably, one or more times at 150 to 300 mg/kg (body weight), of the active ingredient, 2'-fucosyllactose. However, the dosage is provided merely as an example for illustration and may be changed depending on the condition of the patient and the physician's prescription. The pharmaceutical composition may be administered once a day or several times a day, divided into multiple doses a week or month.

In addition, the pharmaceutical composition of the present invention may be administered as a single therapeutic agent or in combination with other therapeutic agents, sequentially or simultaneously with conventional therapeutic agents. Taking into consideration these factors, it is important to administer the composition in the minimum amount sufficient to achieve maximum efficacy without side effects, which can be easily determined by those skilled in the art.

As used herein, the term "prevention" refers to any action that suppresses or delays the onset of hair loss by administration of the pharmaceutical composition according to the present invention.

As used herein, the term "treatment" refers to any action that ameliorates or beneficially changes symptoms due to hair loss by administration of the pharmaceutical composition according to the present invention.

Meanwhile, experimentation was performed (in vivo) on a mouse model treated with 2'-FL in the following. The result showed that hair growth and length significantly increased and hair loss area decreased compared to the testosterone-administered group and the cuticle layer damaged by testosterone administration was also restored. In addition, the result also showed that 2'-FL exhibits these effects without affecting the body weight, liver, and prostate weight of the mouse model, which means that 2'-FL has no negative effect on normal growth. In addition, mouse skin tissue was stained and observed. The result showed that the mouse model (in vivo) treated with 2'-FL exhibited an increase in number and size of hair follicles and improvement in the protein expression of beta-catenin related to hair growth and the gene expression of growth factors related to hair growth, compared to the testosterone-administered group.

Therefore, it was identified by the present invention that treatment with 2'-fucosyllactose is effective in promoting hair growth and ameliorating, preventing or treating hair loss, the present invention is improved in that such identification was actually performed through animal experiments, and the present invention is applicable to various food compositions and pharmaceutical compositions.

Hereinafter, the present invention will be described in more detail with reference to the following examples, but the scope of the present invention is not limited to the examples and includes variations and technical concepts equivalent thereto.

Example 1: Evaluation of Effects of 2'-fucosyllactose Administration on Hair

In this example, the effects of 2'-fucosyllactose administration on hair was determined through in vivo experiments.
1) Animal Model Setup
Eight male mice (B6CBAF1/j, 6 weeks old) were classified into each group and each group was fed chow diet. The experiment was conducted for 24 weeks by subcutaneous injection and oral administration to each group 5 times a week and details of each group were as follows: Subcutaneous injection of 100 µl of vehicle (1% carboxymethylcellulose) and oral administration of PBS were performed on a normal control, subcutaneous injection of testosterone (0.5 mg/day) and oral administration of 100 µl vehicle (PBS) were performed on a negative control, and subcutaneous injections of testosterone (0.5 mg/day) and finasteride (5α-reductase inhibitor, 0.5 mg/kg mouse/day) were performed on a positive control. The 2'-FL-administered group was administered at two concentrations: 1) 2'-FL low-concentration group: subcutaneous administration of testosterone 0.5 mg/day and oral administration of 2'-FL 150 mg/kg mouse/ 100 µl, and 2) 2'-FL high-concentration group: subcutaneous administration of testosterone 0.5 mg/day and oral administration of 2'-FL 300 mg/kg mouse/100 µl. In the following, several experiments related to effects on hair were performed using the mouse model set forth above.
2) Hair, Body Weight, Liver and Prostate Tissue Weight Analysis
2-1) Hair Analysis (Hair Condition, Length, Hair Loss Area and Cuticle Analysis)
To analyze the hair of the mice, the condition of the hair was observed by hair imaging for each experimental animal group once a week. As can be seen from FIG. 1, the result showed that the hair of the 2'-FL-administered group is glossier than that of the control injected only with testosterone.

Figure 2:
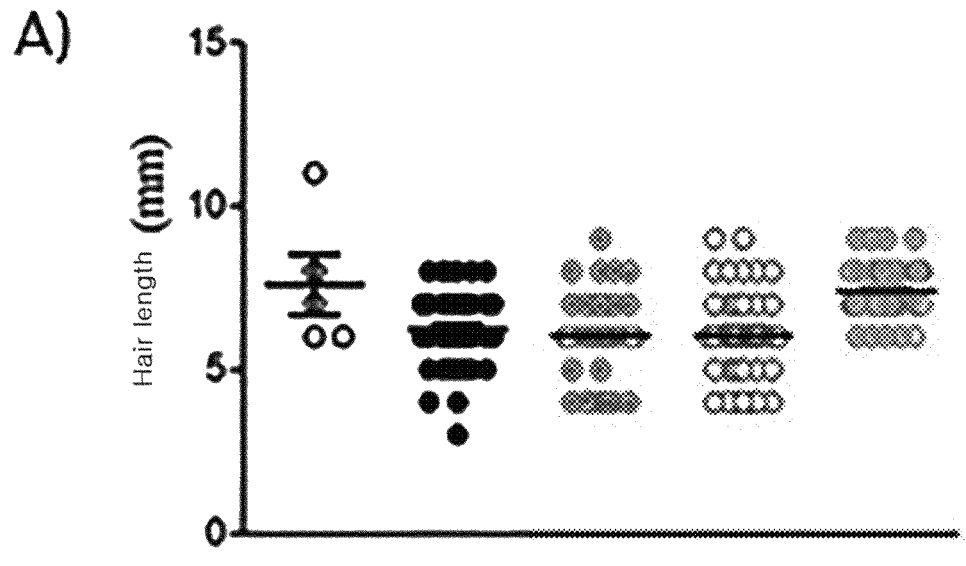
FIG. 2 is a graph showing the change in hair length of the mouse model treated with 2'-fucosyllactose according to the present invention.
Figure 2:
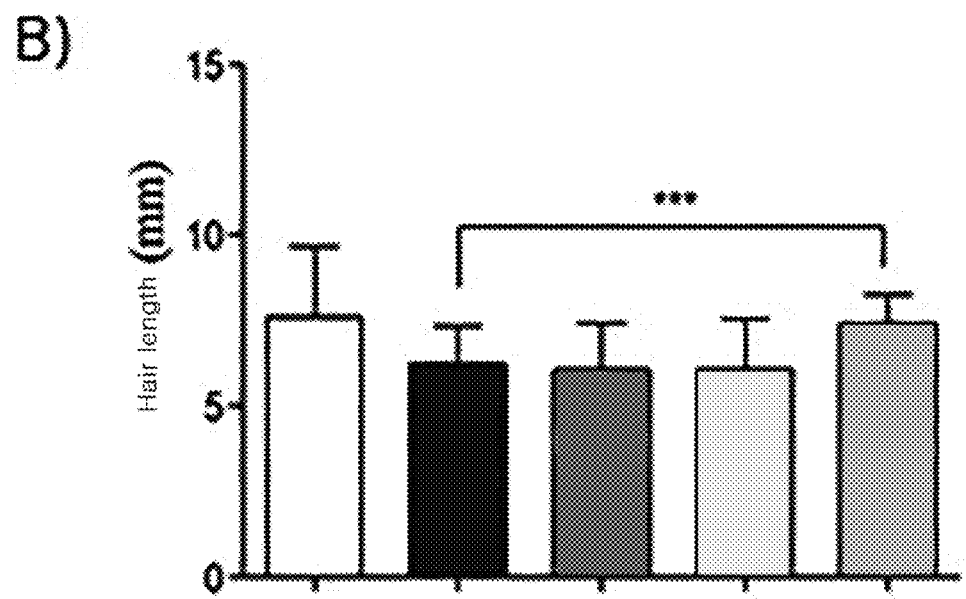

After the completion of the 24-week experiment, the hair obtained by dissection based on autopsy was observed with a microscope to measure the length of the hair. The lengths of the hairs of respective mice were measured and an average of the lengths was calculated. As a result, as can be seen from FIG. 2, the 2'-FL-administered group exhibited a significant concentration-dependent increase in hair length compared to the normal control (vehicle) and the control injected only with testosterone.

Figure 3:
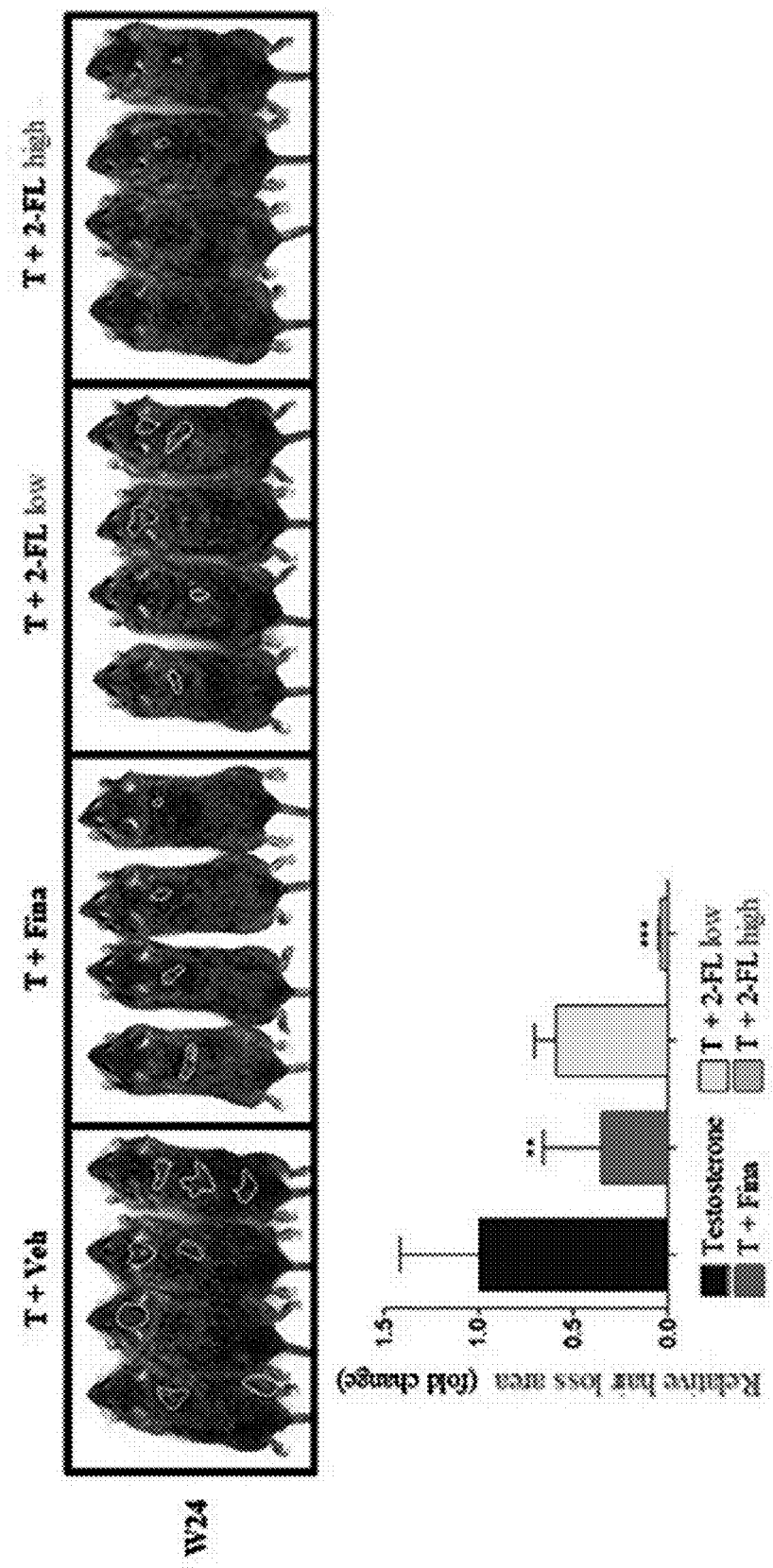
FIG. 3 is a graph showing the hair loss area of the mouse model treated with 2'-fucosyllactose according to the present invention.

The results of analysis of the hair loss area of mice under a microscope showed that the hair loss area of the 2'-FL-administered group decreased in a concentration-dependent manner compared to the control injected only with testosterone, as shown in FIG. 3. In particular, the 2'-FL high-concentration group exhibited a decrease in hair loss area compared to the positive control (testosterone+finasteride).

Figure 4:
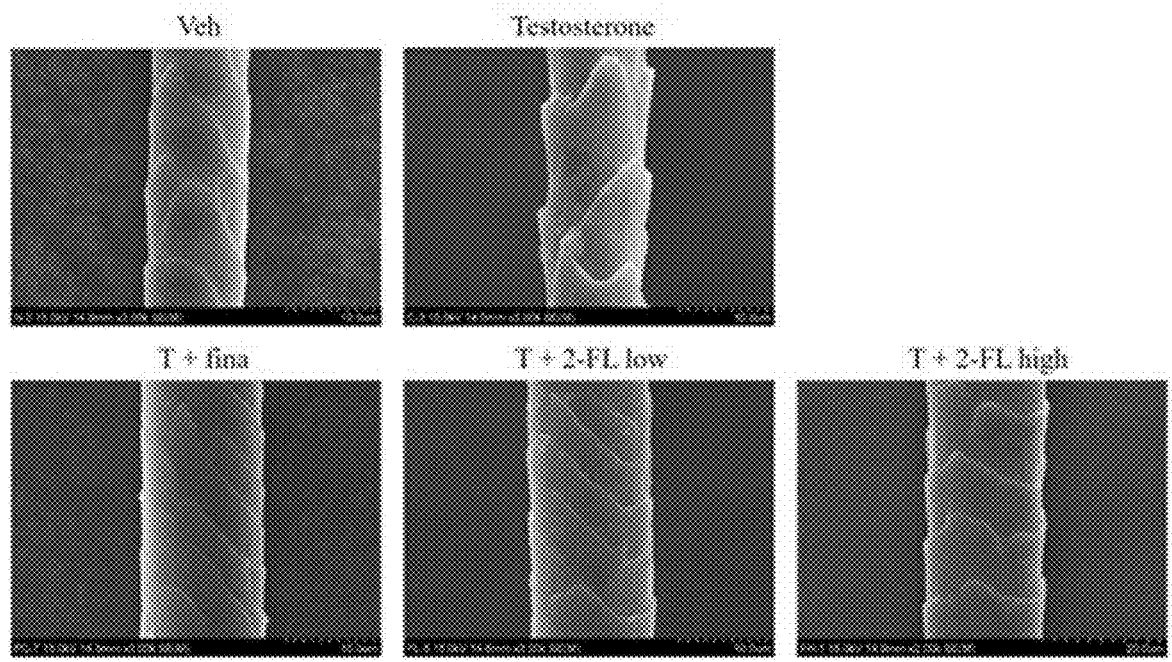
FIG. 4 is a graph showing the hair cuticle layer of the mouse model treated with 2'-fucosyllactose according to the present invention.
Figure 5:
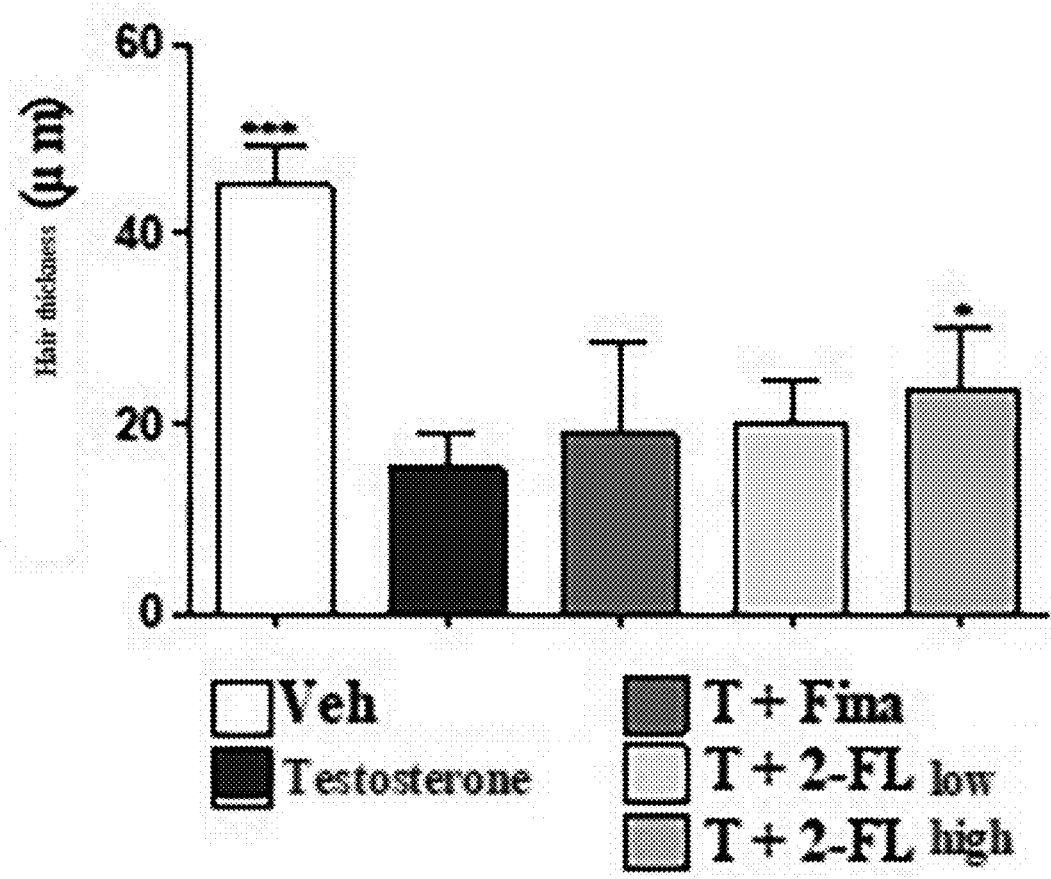
FIG. 5 is a graph showing the hair thickness of the mouse model treated with 2'-fucosyllactose according to the present invention.

The degree of damage to the cuticle in hair obtained by dissection based on autopsy was measured using a scanning electron microscope (SEM). The result showed that, compared to the control injected with only testosterone, as shown in FIG. 4, the hair cuticle of the 2'-FL high-concentration group was improved as much as the normal control, which is consistent with the result of hair gloss improvement of the 2'-FL-administered group in FIG. 1. In addition, the result of analysis of the mouse hair thickness as shown in FIG. 5 showed that the hair thickness of the 2'-FL high-concentration group significantly increased compared to the control injected with only testosterone.

Figure 6:
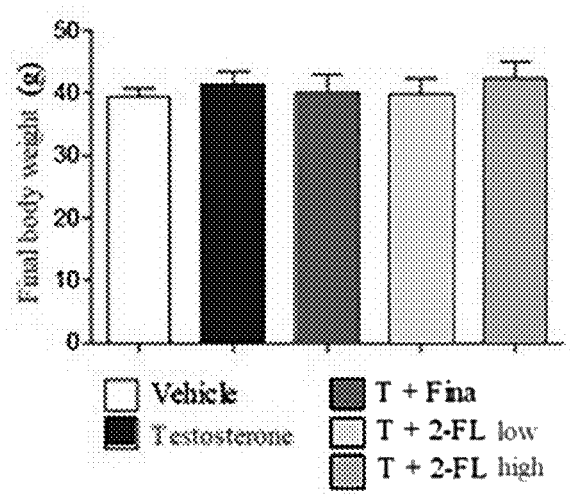
FIG. 6 is a graph showing the tissue weight of the mouse model treated with 2'-fucosyllactose according to the present invention (in the order of body weight, liver, and prostate)
Figure 6:
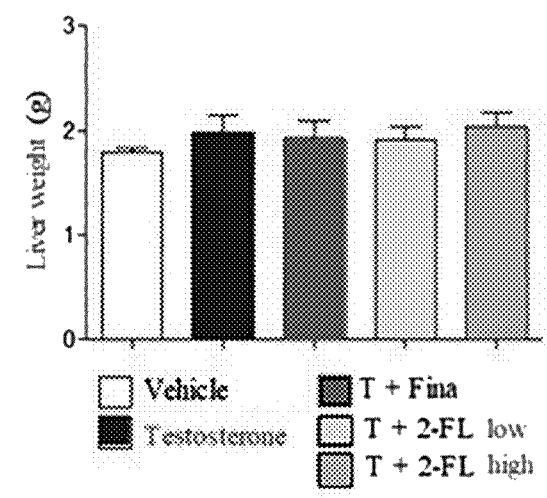
Figure 6:
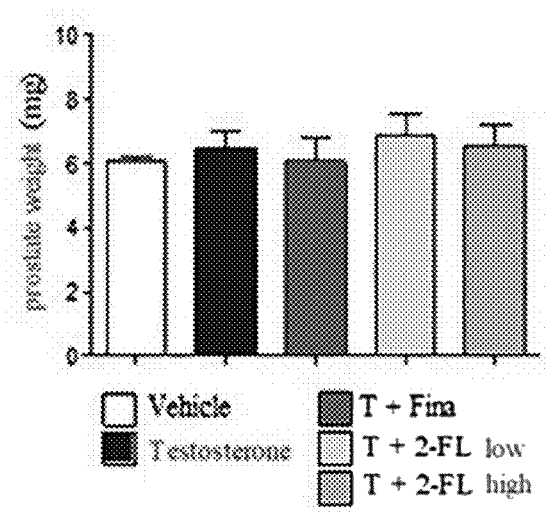

After the completion of the 24-week experiment, the weight of body weight, liver, and prostate tissue was measured. As can be seen from FIG. 6, administration of 2'-FL caused neither change in body weight nor liver or prostate tissue size or weight, which indicates that 2'-FL has no negative effects on major metabolic tissues related to hair loss.

Figure 7:
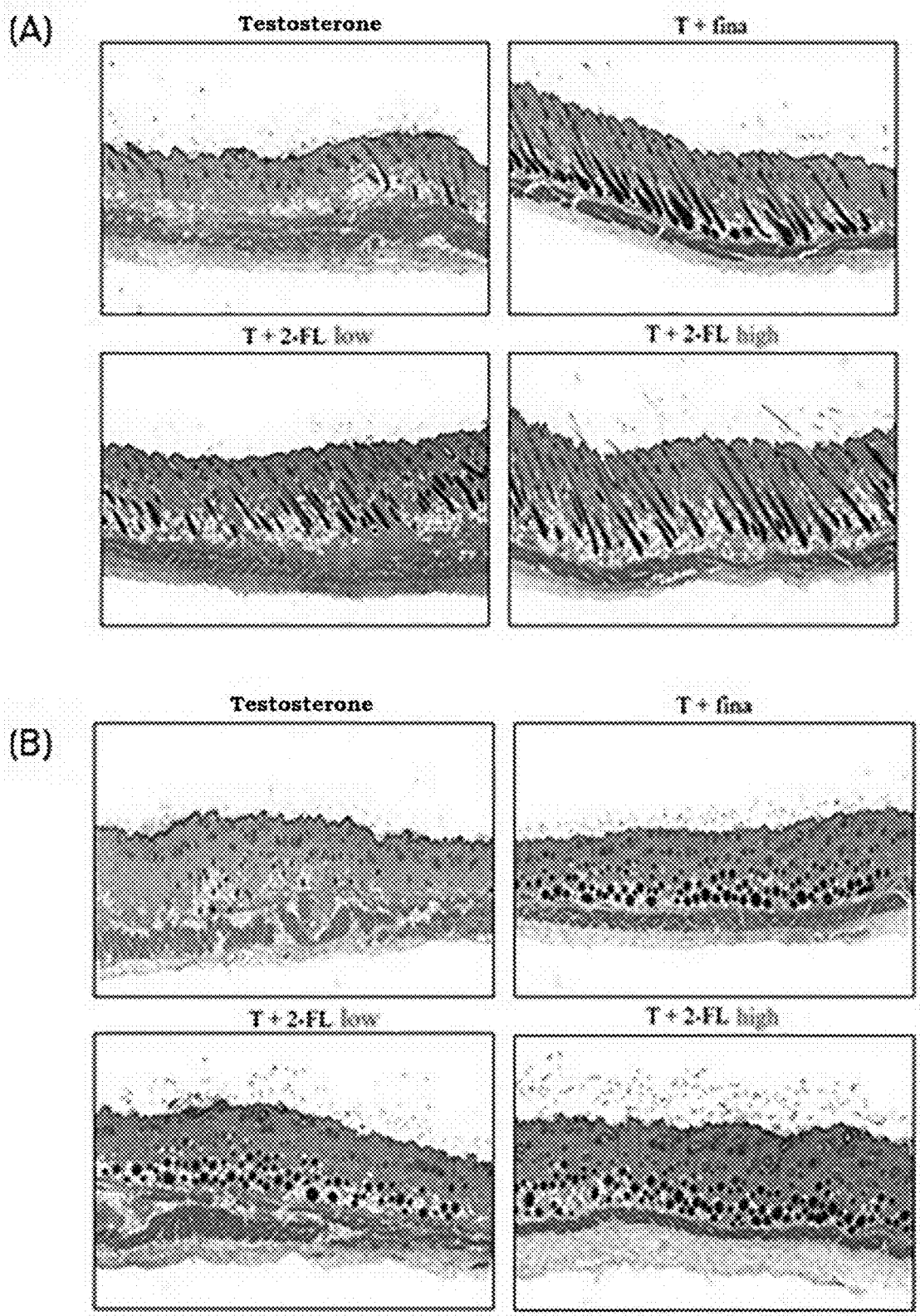
FIG. 7 is an image showing results of the side (A) and front (B) H&E staining of skin tissue of the mouse model treated with 2'-fucosyllactose according to the present invention.
Figure 8:
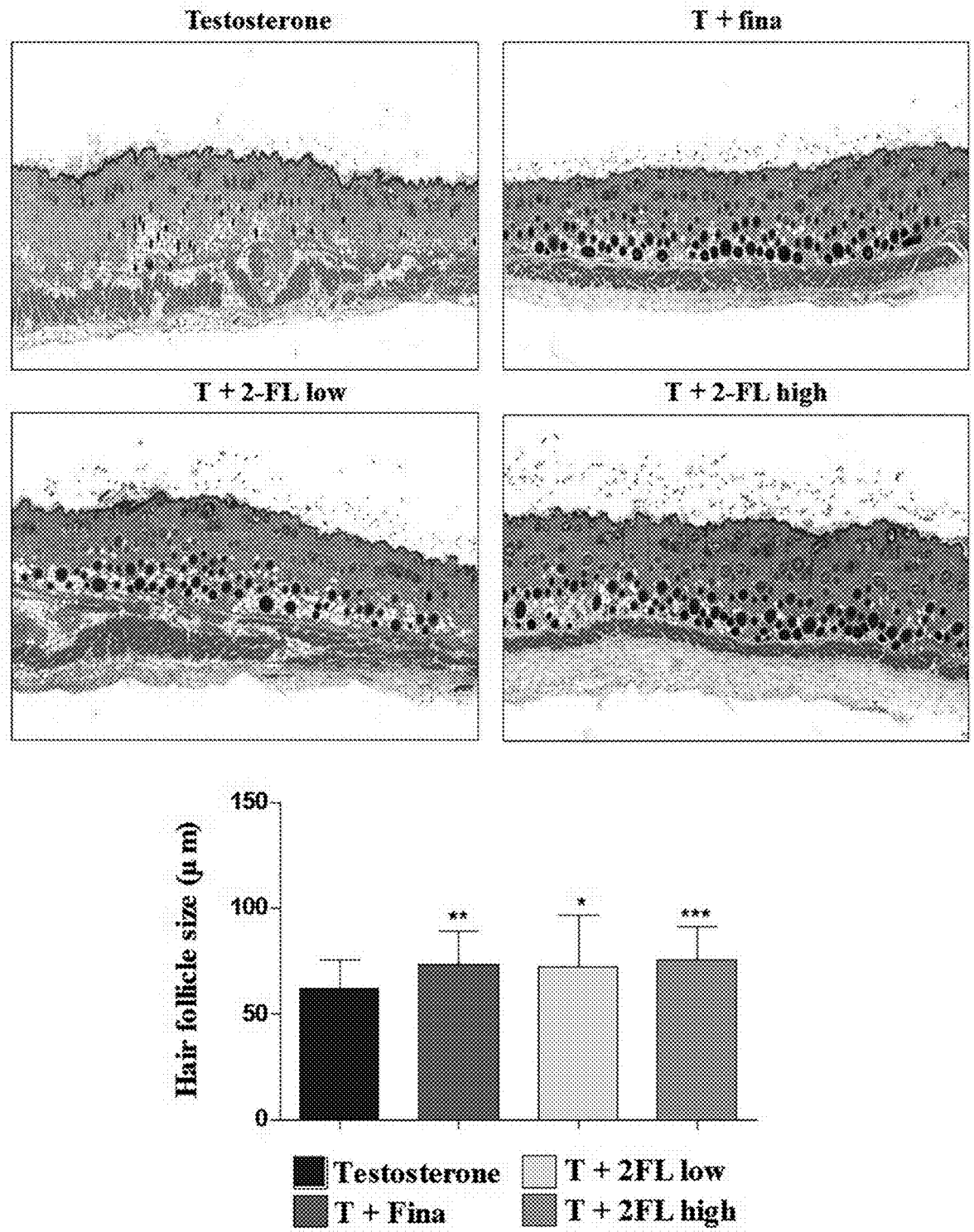
FIG. 8 is an image and graph showing the size of skin tissue hair follicles in the mouse model treated with 2'-fucosyllactose according to the present invention.

3) Skin Tissue Analysis and Confirmation of Hair Proliferation and Growth-Related Marker Proteins and Gene Expression in Skin Tissue After the completion of the 24-week experiment, H&E staining (hematoxylin-eosin staining) was performed to analyze skin tissue extracted through autopsy and the process was as follows: the beeswax was dewaxed, dehydrated, treated with hematoxylin-eosin, differentiated, subjected to bluing, treated with eosin, dehydrated, removed, and coverslipped. The H&E-stained skin tissue was analyzed. The result showed that, as can be seen from FIG. 7 (A: side, B:

front) and FIG. 8, the 2'-FL-administered group exhibited increased growth phase hair and increased number and size of hair follicles, compared to the control treated with only testosterone.

The expression of hair growth-related marker proteins in the skin tissue obtained above was analyzed. The Wnt/beta-catenin (β-catenin) signaling system is known to be a key mechanism in the hair growth regulation process and is used as an important parameter in determining the efficacy of ameliorating genetic hair loss. For this purpose, proteins were extracted using RIPA lysis buffer (Thermo Scientific, USA) and centrifuged at 4° C. and 3,000 rpm for 10 minutes. The supernatant obtained by centrifugation was assayed through BCA protein assay (Thermo Scientific, USA) and electrophoresed on SDS-polyacrylamide gel, and the gel was transferred to a PVDF membrane (Trans-Blot, BioRad Laboratories). The membrane obtained by transfer was blocked with 5% skim milk. A primary antibody was linked to the result, followed by incubation at 4° C. overnight and washing with 1×TBST. Then, a secondary antibody was linked thereto, followed by incubation at room temperature for 1 hour and detection. The result was washed with 1×TBST and ECL solution was added thereto, followed by detection.

Figure 9:
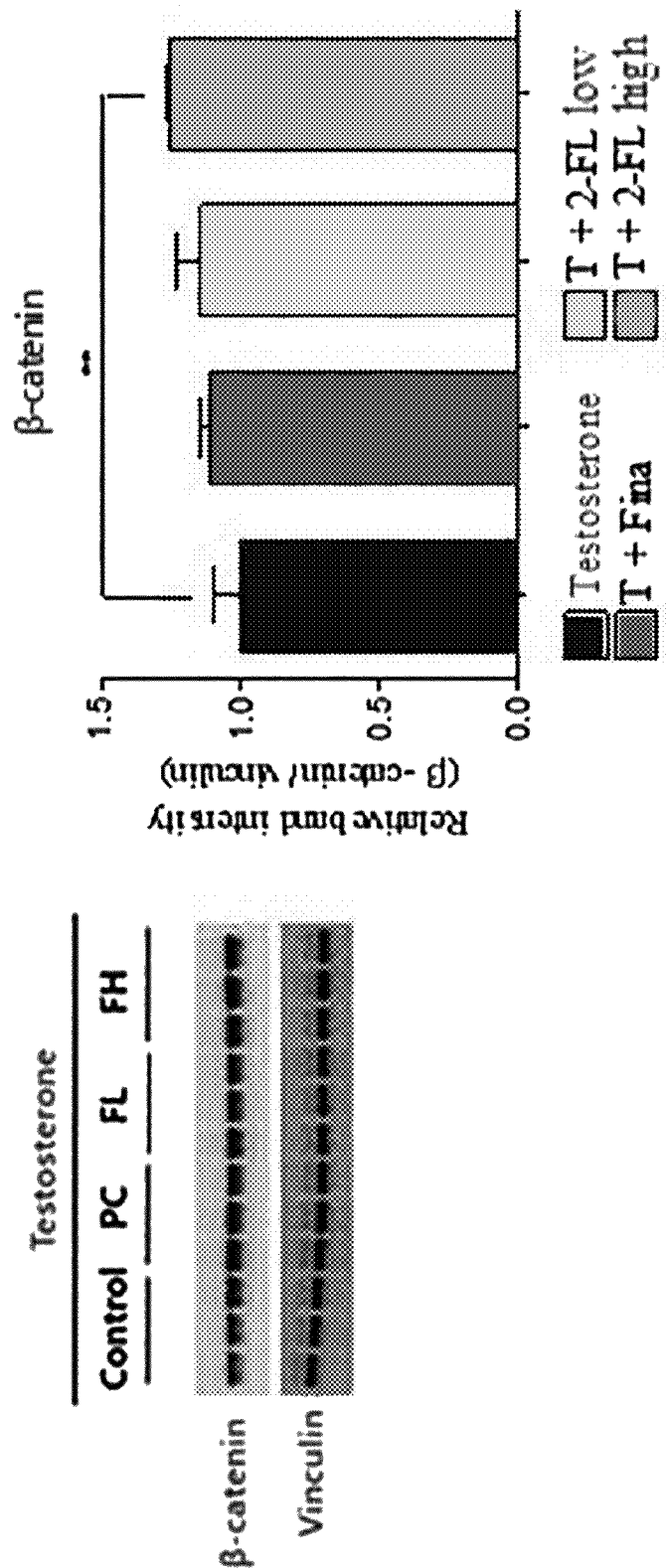
FIG. 9 shows expression patterns of the hair growth-related protein beta-catenin (β-catenin) in the skin tissue of the mouse model treated with 2'-fucosyllactose according to the present invention.

The expression of proteins related to hair growth was observed. As can be seen from FIG. 9, the result showed that protein expression of beta-catenin related to hair growth increased compared to the negative control treated only with testosterone and that the 2'-FL high-concentration group exhibited significantly increased expression.

Meanwhile, the expression of hair growth-related marker genes in the skin tissue obtained above was analyzed. Growth factors related to hair growth include EGF (epidermal growth factor), TGF-α (transforming growth factor-α), TGF-β1 (transforming growth factor-β1), KGF (keratinocyte growth factor), IGF-1 (insulin-like growth factor-1), HGF (hepatocyte growth factor), VEGF (vascular endothelial growth factor) and FGF (fibroblast growth factor) family. To analyze expression of IGF-1, VFGF, and FGF genes thereamong, skin tissue was pulverized using an MP device, and RNA was extracted using an RNeasy mini kit (Qiagen, USA). CDNA synthesis was performed using the ReverTra Ace™ qPCR RT Kit (Toyobo, Japan) and RT-qPCR was performed using SYBR Green master mix (Toyobo, Japan).

Figure 10:
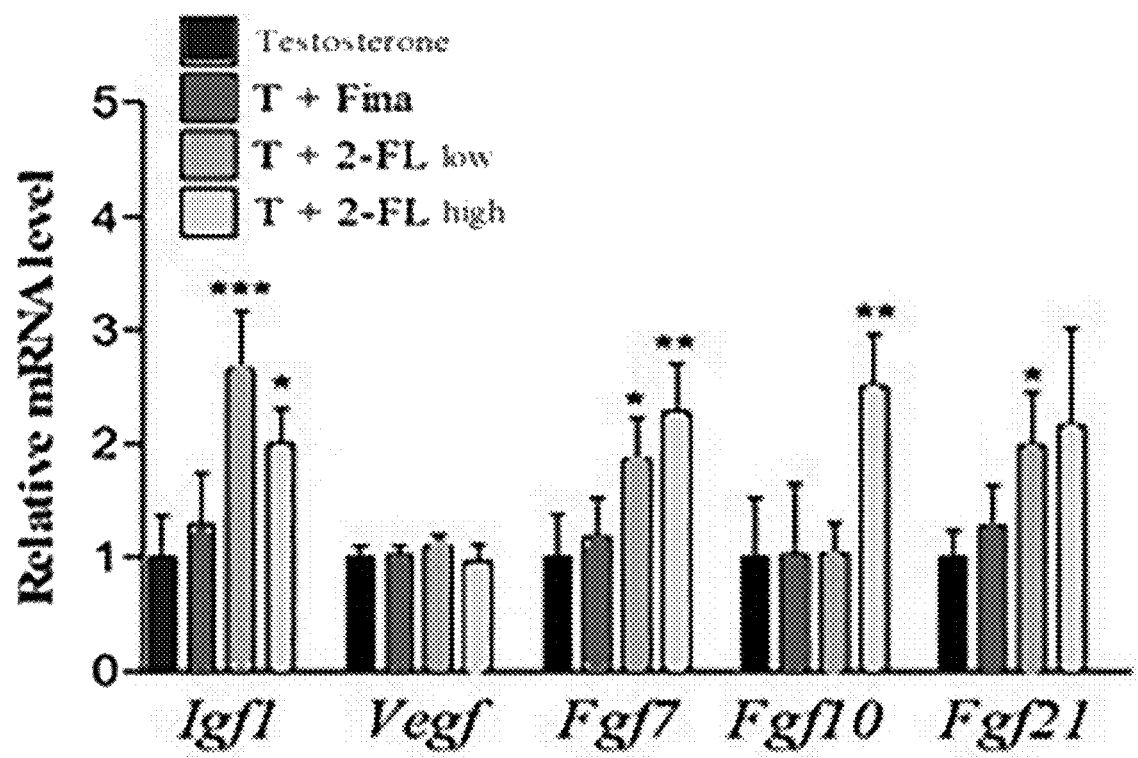
FIG. 10 shows expression patterns of hair growth-related genes (IGF, VEGF, and FGF) in skin tissue of the mouse model treated with 2'-fucosyllactose according to the present invention.

The result of gene expression analysis of growth factors related to hair growth showed that 2'-FL administration improved gene expression, as shown in FIG. 10. In particular, the 2'-FL-administered group exhibited significantly improved gf1 and Fgf7 gene expression compared to the testosterone control, the 2'-FL high-concentration group exhibited significantly improved Fgf10 gene expression, and the 2'-FL low-concentration group exhibited significantly improved Fgf21 gene expression.

As apparent from the foregoing, the present invention provides treatment with a combination of testosterone and 2'-fucosyllactose that increases hair gloss, increases hair length, reduces hair loss area, enhances hair cuticles, increases the number and size of hair follicles, and improves expression of proteins and genes related to hair proliferation and growth, compared to treatment with testosterone alone, thus being applicable as a substance for various food and pharmaceutical compositions based on the effects of promoting hair growth, improving hair loss, and ameliorating, preventing or treating hair loss.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for (i) promoting hair growth, and (ii) enhancing hair cuticles or increasing a number and size of hair follicles in a subject with androgenetic alopecia, the method comprising administering to the subject 2'-fucosyllactose.

2. A method for (i) ameliorating, preventing or treating androgenetic alopecia, and (ii) enhancing hair cuticles or increasing a number and size of hair follicles, the method comprising administering to a subject in need thereof 2'-fucosyllactose.

3. The method according to claim 1, wherein the 2'-fucosyllactose is in an amount of 150 to 300 mg/kg based on a body weight.

4. The method according to claim 2, wherein the 2'-fucosyllactose is in an amount of 150 to 300 mg/kg based on a body weight.

* * * * *